United States Patent [19]

Sciarra

[11] Patent Number: 4,551,149
[45] Date of Patent: Nov. 5, 1985

[54] PROSTHETIC VISION SYSTEM

[75] Inventor: Michael J. Sciarra, 59 Far Pond Rd., Southampton, N.Y. 11968

[73] Assignee: Michael Sciarra, Southampton, N.Y.

[21] Appl. No.: 349,179

[22] Filed: Feb. 16, 1982

[51] Int. Cl.$^4$ .......................... A61F 1/16; A61F 1/24; A61N 1/04
[52] U.S. Cl. ......................................... 623/4; 623/24; 128/784; 340/407
[58] Field of Search .................................. 3/13, 1, 1.1; 128/419 R, 784; 340/407

[56] References Cited

U.S. PATENT DOCUMENTS 2,721,316 10/1955 Shaw ...................................... 3/1 X

FOREIGN PATENT DOCUMENTS 1286316 8/1972 United Kingdom ...................... 3/13
2016276 9/1979 United Kingdom ....................... 3/1

OTHER PUBLICATIONS

Fulton, Physiology of the Nervous System, 1943, pp. 324-331.
Buchanan, Functional Neuro-Anatomy, Philadelphia, Lea and Febiger, pp. 85-86, 104-110.
Mechanics Illustrated, Electronic Vision, Jul. 1981, p. 62.
"Introduction to Sensory Prostheses for the Blind and Deaf", by W. H. Dobelle, Trans. Amer. Soc. Artif. Int. Organs, vol. XX, 1974, pp. 761-764.
"Artificial Vision for the Blind: Electrical Stimulation of Visual Cortex Offers Hope for a Functional Prosthesis", Science, vol. 183, Feb. 1974, pp. 440-444.
"Phosphenes Produced by Electrical Stimulation of Human Occipital Cortex, and Their Application to the Development of a Prosthesis for the Blind", by W. H. Dobelle et al., Journal of Physiology, (1974), 243, pp. 553-576.
"Braille Reading by a Blind Volunteer by Visual Cortex Stimulation", Nature, vol. 259, Jan. 15, 1976, pp. 111-112.
"Fabrication of Large Arrays of Cortical Electrodes for Use in Man", by G. F. Klomp et al., Journal of Biomedical Materials Research, vol. 11, pp. 347-364, 1977.
"The Relationship Between Stimulus Parameters and Phosphene Threshold/Brightness, During Stimulation of Human Visual Cortex", by D. C. Henderson et al., Trans. Amer. Soc. Artif. Internal Organs, vol. XXV, 1979, pp. 367-371.
"Mapping the Representation of the Visual Field by Electrical Stimulation of Human Visual Cortex", by W. H. Dobelle et al., Amer. Journal of Ophthalmology, 88: 727-735, 1979.
"Artificial Vision for the Blind by Electrical Stimulation of the Visual Cortex", by W. H. Dobelle et al., Neurosurgery, vol. 5, No. 4, 1979, pp. 521-527.

Primary Examiner—Ronald L. Frinks
Attorney, Agent, or Firm—Pasquale A. Razzano

[57] ABSTRACT

A prosthetic vision system is provided with a lens implanted in an ocular socket to focus light onto a coherent fiberoptic bundle. The fiberoptic bundle conveys the received light to photovoltaic semiconductors mounted in a gate array. The gate array is mounted in the region of the calcarine fissure in the user's cortex. The photovoltaic semiconductors stimulate the optic tract or visual cortex much in the manner done in a person having sight.

15 Claims, 4 Drawing Figures

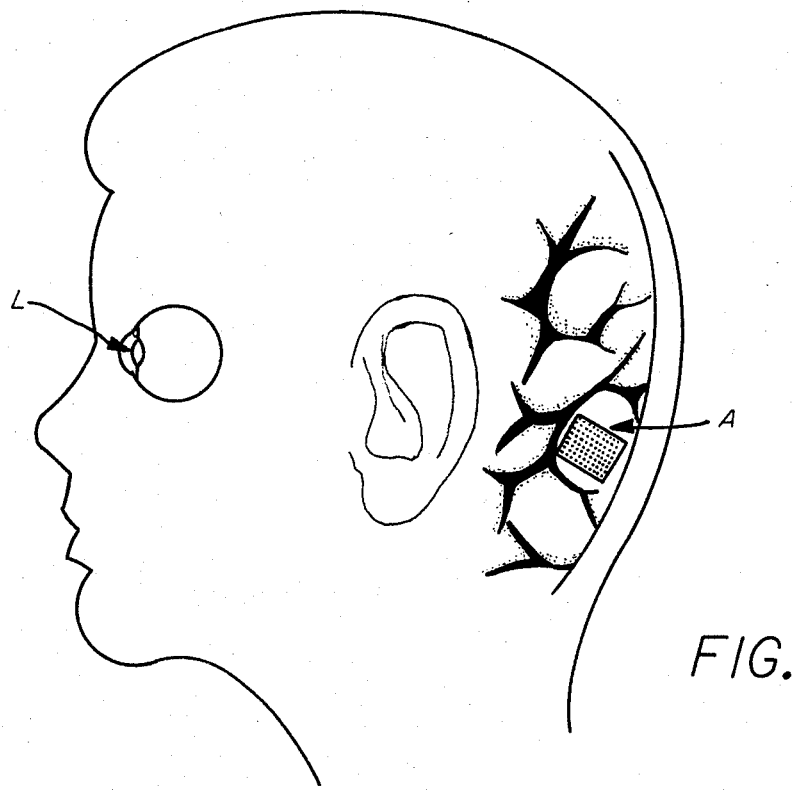
FIG. 1
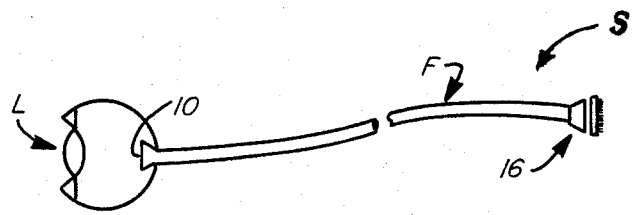
FIG. 2
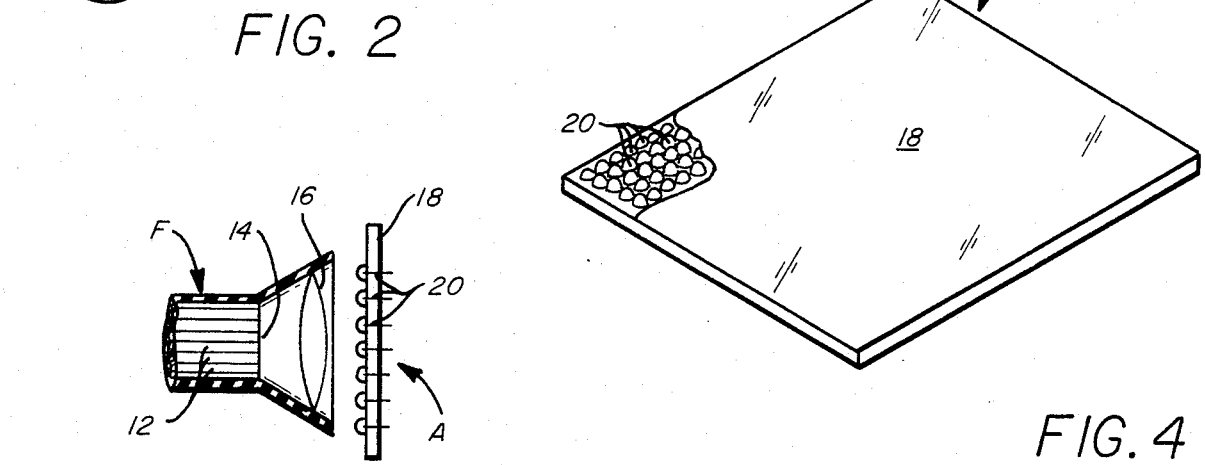
FIG. 3
FIG. 4

PROSTHETIC VISION SYSTEM

BACKGROUND OF INVENTION

1. Field of Invention

The present invention relates to prosthetic vision systems.

2. Description of Prior Art

Millions of people are blinded by diseases of the eye. Most of these people suffer from pathology relating to the eye itself, in particular to diseases which either affect the retina directly, such as tumors, or cause the retina to be damaged, such as in the case of glaucoma. Essentially though, the visual centers of the cerebral cortex are still operative in over ninety percent of these cases. This has been exhaustively demonstrated through the direct stimulation of the visual cortex using microprobes which cause the patient to announce that bursts of color or flashes of light or the like are perceived or "seen". In particular, with the proper placement of electrodes actual geometric shapes such as triangles, circles, and other primitive shapes have been observed in previously sightless individuals. The limiting factors in the past have been several.

Alignment of electrodes with the cerebral cortex was one of these factors. As the visual cortex is one of the few areas of the cortex which has a one to one mapping of the retina it becomes a critical factor that any attempt to stimulate this area meaningfully must start with an ordered array of electrodes. This means that the spacing between individual electrodes must be equal, and the effect of one electrode upon the other minimized.

Another factor was density of the cortex stimulating electrodes. In the past, approximately twenty electrodes have been manually placed on the visual cortex. This has required the use of large computers to sort out the signals and put them in an order that could be recognized. Susequently, a television camera tube would then transfer the "image" through a computer to the brain. Such an approach, although helpful for experimental purposes, was cumbersome and unwieldy. Finally, other factors have included fibrosis being noted around areas where electrodes were implanted and overstimulation of brain cells.

SUMMARY OF INVENTION

Briefly, the present invention provides a new and improved prosthetic vision system for a blind or otherwise vision-impaired user. Optic conditions or light levels are received and sensed by means of a lens, preferably implanted in an ocular socket of the user. The light sensed by the lens is focused onto fiberoptic conductor cables which transfer sensed optical conditions to an electrode array which stimulates the visual cortex of the user. In this manner, those portions of the brain of the vision-impaired user which would receive stimuli but for the vision impairment receive electrical signals as if no vision impairment existed. The fiberoptic conductor cables are arranged into coherent bundles so that the portions of the electrode array which are energized correspond to the portions of the lens which receives light, materially reducing the complexity of experimental structures attempted in the past and making computer processing of the signals which are optically sensed no longer required.

BRIEF DESCRIPTION OF THE DRAWINGS

FIGS. 1 and 2 are schematic diagrams, not to scale, of the prosthetic vision system of the present invention;

FIG. 3 is an elevation of a portion of the system on FIGS. 1 and 2; and

FIG. 4 is an isometric view of a portion of the structure shown in FIGS. 1, 2 and 3.

DESCRIPTION OF PREFERRED EMBODIMENT

In the drawings, the letter S designates generally a prosthetic vision system according to the present invention for assisting vision-impaired or blind users in seeing. Although principally intended for use with humans, the present invention might as well be used in animals, particularly in experiments, and thus the term user as used throughout this application is intended to include both human and animals.

The system S includes a lens L and an electrode array A which is optically connected to the lens L by a fiberoptic conductor bundle F. Preferably, a lens, electrode and fiberoptic bundle are provided for both eyes where needed. The lens L receives and senses optic conditions or light levels presented to the user and focuses the sensed optic images onto a first input end 10 of each of a plurality of individual optic fibers 12 in the fiberoptic bundle F. The ends 10 of the fiberoptic bundle F are formed into a polished common planar surface so that the optic conditions focused thereon by the lens L are in effect partitioned into a matrix of small individual areas. The intensity of the light in each of those areas is determined by the intensity of the light in the optic conditions presented to the lens L.

The lens L may be mounted or implanted in an ocular socket or elsewhere, as desired. If implanted in a user, the lens L is, of course, formed from a material acceptable to body tissues. The lens L is transparent and may be formed to contain a material, such as a silver halide composition, which darkens when exposed to ultraviolet light. Such a material is of the type commonly used in commercially available eyeglasses. With the lens L formed of such a material, the amount of light transmitted through the fiberoptic bundle F is limited and the level of said signal formed in the electrode array A to stimulate the cortex region of the user's brain is lowered.

The fiberoptic bundle F is formed from the number, usually six to nine hundred, of individual light conducting optic fibers or light guides which convey light intensity conditions sensed and focused thereon by the lens L to the electrode array A. The individual light conducting optic fibers 12 each terminate in a second or output end 14 in proximity to the electrode array A. The output ends of the fiberoptic conductors 12 are arranged in a corresponding matrix to the matrix formed by the input ends 10 and the individual optic fibers 12 thus form a coherent light guide. With the fiberoptic bundle F formed as a coherent light guide with the present invention, shades of darkness and lightness in an image received on the lens L are focused onto the front end 10 of the fiberoptic bundle F and are transported to the output ends 14 in a matrix corresponding to the image received. Thus, an image imposed by the lens F onto the front ends 10 is reproduced at the second or output end 14 of the fiberoptic bundle F.

The image present at the output ends 14 of the cables 12 of the fiberoptic bundle F is focused by a second lens 16 onto the electrode array A. The electrode array A is in the form of an electrically conductive, flexible semiconductor substrate of relatively small dimensions, such as one square centimeter, so that one for each lens L may be implanted in the optical cortex region of the calcarine fissure in the brain of the user using the prosthetic vision system S. Portions of the cables 12, as well as the lens 16, are also implanted in this location. Portions of fiberoptic bundle F not inside the user's skull may be subcutaneously implanted, if desired. If power consumption requirements dictate, the electrode array A is electrically connected to a suitable power source or battery, preferably external to the skull of the user. The fiberoptic bundle F and lens 16 are encapsulated in a medical grade silicone rubber coating 18, such as the type sold under the trademark "Silastic". Electrode array A is coated with a carbon-impregnated conductive silicone.

An array of rows and columns of miniturized photovoltaic semiconductor cells or phototransistors 20 is formed on at least one surface of the substrate in the electrode array A. The phototransistors 20 are preferably of the PN type which when luminous energy in the form of photons from the fiberoptic bundle output ends 14 impinges upon them, convert the luminous energy to electrical energy. The phototransistors 20 when energized form a potential which passes through the conductive coating 18 and energizes neurons of the visual cortex of the user's brain. The array of rows and columns of miniature phototransistors 20 of the electrode array A corresponds to the array or matrix of input and output ends of the fiberoptic bundle F so that a numerical correspondence, such as a one-to-one, exists between the matrix into which the optic conditions sensed by the lens L is divided and the number of phototransistors 20 rendered conductive when exposed to light from the fiberoptic bundle F. The phototransistors 20 are miniaturized components and are spaced from each other so that each conductive one of them can energize preferably three or less neurons in the user's visual cortex in response to light from one of the fibers 12. The photodiodes are preferably laser trimmed so that their N regions are directly exposed through the conductive coating 18 to neurons in the user's cortical area of vision. Thus when the phototransistors are energized, neural stimulation occurs.

Portions of the visual region in the user's brain which are stimulated correspond to portions of the lens L which sense light conditions. In order to prevent overstimulation of those portions of the user's brain when confronted with high intensity light conditions, the electrode array A may be time-gated by a suitable switching circuit set to activate the array A at intervals greater then the polarization, de-polarization time or the absolute refractory period in the user's brain to permit the cells to return to their normal state.

Medical treatises indicate that macular representation is more precisely organized than any other bodily sensory system, and further that there is a point-to-point relationship between the retina and the occipital lobe, without significant spatial overlapping. Further, medical treatises have indicated that electrical stimulation of the visual cortex in a conscious subject gives rise to impressions of pin-points of light in corresponding loci in the fields of vision. Further, the treatises indicate that stimulation of the peristriate area produces integration to the extent of organization of the more primitive impression elicited from the visual cortex area into geometric figures. Finally, the treatises indicate that stimulation of other areas of the user's brain introduces color and definitive form of familiar objects. Finally, research has confirmed in the published literature that experiments have permitted a blind volunteer to see simple geometrical shapes.

The present invention takes cognizance of these physical phenomena. The input ends of the fiberoptic bundle F effectively partition a field of view presented to the lens L into a matrix of small individual areas, and the intensity of the light in those areas is conveyed to the electrode array A. Individual ones of the phototransistors in the array A are selectively energized where sufficient light intensity is sensed by the lens L and portions of the user's visual cortex then stimulated. In this manner, a vision-impaired user's brain is presented with physical stimuli of the type which occur in a human or animal having normal vision. This occurs, even though the user's eyes or optic nerves or both are damaged to an extent that normal vision does not occur.

The foregoing disclosure and description of the invention are illustrative and explanatory thereof, and various changes in the size, shape, materials, components, circuit elements, wiring connections and contacts, as well as in the details of the illustrated circuitry and construction may be made without departing from the spirit of the invention.

I claim:

1. A prosthetic vision system for a vision-impaired user, comprising:
   (a) lens means for receiving and sensing optic conditions;
   (b) electrode array means adapted to be implanted on the visual cortex of the user's brain for stimulating the visual cortex of the user in response to the sensed optical conditions; and
   (c) fiberoptic conductor means for transferring the sensed optic conditions from said lens means directly to said electrode array means on the visual cortex.

2. The system of claim 1, wherein said fiberoptic conductor means comprises:
   a plurality of individual fiber light guides formed into a coherent light bundle.

3. The system of claim 1, wherein:
   said fiberoptic conductor means is encapsulated in a conductive medical grade silicone rubber.

4. The system of claim 1, wherein:
   said electrode array means is of a size permitting implantation in the region of the calcarine fissure of the user.

5. The system of claim 1, wherein:
   said lens means is of a size permitting installation in an eye socket of the user.

6. A prosthetic vision system for a vision-impaired user, comprising:
   (a) lens means for receiving and sensing optic conditions;
   (b) electrode array means for stimulating the visual cortex of the user in response to the sensed optical conditions; and
   (c) fiberoptic conductor means for transferring the sensed optic conditions from said lens means to said electrode array means; said electrode array means comprising means for converting luminous energy sensed by said lens means into electrical energy; and means for transferring the electrical energy to the visual cortex of the user.

7. The system of claim 6, wherein:

(a) said means for transferring comprises a conductive substrate having a plurality of electrodes for transferring electrical energy to neurons in the visual cortex of the user; and (b) said means for converting luminous energy comprises a plurality of phototransistors mounted in an array of rows and columns on said conductive substrate.

8. A prosthetic vision system for a vision-impaired user, comprising:

(a) lens means for receiving and sensing optic conditions;

(b) electrode array means for stimulating the visual cortex of the user in response to the sensed optical conditions; and (c) fiberoptic conductor means for transferring the sensed optic conditions from said lens means to said electrode array means; said electrode array means comprising, a plurality of photovoltaic cells mounted in an array of rows and columns on a conductive substrate.

9. The system of claim 8, wherein:
said photovoltaic cells and said substrate are encapsulated in a conductive medical grade silicone rubber.

10. The system of claim 8, wherein:
said substrate is flexible.

11. The system of claim 10, wherein said electrode array means comprises:

(a) a conductive substrate having a plurality of electrodes for transferring electrical energy to neurons in the visual cortex of the user; and (b) means for converting luminous energy comprising a plurality of phototransistors mounted in an array of rows and columns on said conductive substrate.

12. The system of claim 11, wherein:
said photovoltaic cells are spaced from each other on said substrate so as to stimulate no more than three neurons in the user's cortex for each individual fiber light guide transferring light.

13. A prosthetic vision system for a vision-impaired user, comprising:

(a) lens means for receiving and sensing optic conditions;

(b) electrode array means for stimulating the visual cortex of the user in response to the sensed optical conditions; and (c) fiberoptic conductor means for transferring the sensed optic conditions from said lens means to said electrode array means; said fiberoptic conductor means comprising, a plurality of individual fiber light guides having input ends arranged in a matrix to receive light from the sensed optic conditions and further having output ends arranged in a corresponding matrix adjacent said electrode array means.

14. A prosthetic vision system for a vision-impaired user, comprising:

(a) lens means for receiving and sensing optic conditions;

(b) electrode array means for stimulating the visual cortex of the user in response to the sensed optical conditions;

(c) fiberoptic conductor means for transferring the sensed optic conditions from said lens means to said electrode array means; and (d) second lens means for transferring sensed optic conditions from said fiberoptic conductor means to said electrode array means.

15. A prosthetic vision system for a vision-impaired user, comprising:

(a) lens means for receiving and sensing optic conditions;

(b) electrode array means for stimulating the visual cortex of the user in response to the sensed optical conditions; and (c) fiberoptic conductor means for transferring the sensed optic conditions from said lens means to said electrode array means; said lens means including a composition which darkens when exposed to ultraviolet light.

* * * * *